United States Patent [19]
Bisek et al.

[11] Patent Number: 5,305,368
[45] Date of Patent: Apr. 19, 1994

[54] METHOD AND APPARATUS FOR PIECE-WISE RADIOGRAPHIC SCANNING

[75] Inventors: Joseph P. Bisek, Madison; Jixing Chen, Fitchburg, both of Wis.

[73] Assignee: Lunar Corporation, Madison, Wis.

[21] Appl. No.: 36,130

[22] Filed: Mar. 23, 1993

Related U.S. Application Data

[63] Continuation-in-part of Ser. No. 976,797, Nov. 16, 1992, which is a continuation-in-part of Ser. No. 944,626, Sep. 14, 1992, Pat. No. 5,228,068.

[51] Int. Cl.⁵ ............................................. G21K 5/10
[52] U.S. Cl. ................................ 378/146; 378/62; 378/196
[58] Field of Search ............... 378/145, 146, 62, 193, 378/195, 196, 197, 198

[56] References Cited

U.S. PATENT DOCUMENTS

| | | | |
|---|---|---|---|
| 4,709,382 | 11/1987 | Sones | 378/62 |
| 4,811,373 | 3/1989 | Stein | 378/146 X |
| 5,132,995 | 7/1992 | Stein | 378/146 X |
| 5,132,996 | 7/1992 | Moore et al. | 378/62 X |
| 5,177,776 | 1/1993 | Ohmari et al. | 378/146 X |

*Primary Examiner*—David P. Porta
*Attorney, Agent, or Firm*—Quarles & Brady

[57] ABSTRACT

A scanning radiographic densitometer constructs a broad area, two dimensional projection image from a combination of a set of smaller fan beam scans by tilting the axis of each such smaller scan to construct an effective larger fan beam to reduce artifacts caused by height dependant overlap of the multiple fan beams. The data is projected to a non-planar image surface to eliminate local area distortion such as may cause error in density measurements and to permit some overlap without height sensitive effects.

7 Claims, 5 Drawing Sheets

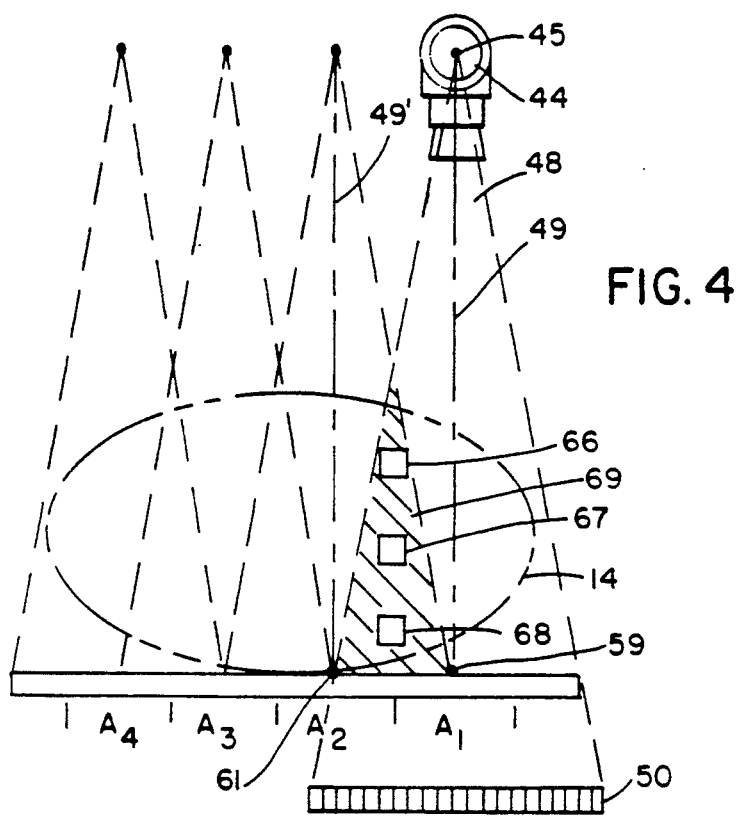
FIG. 4
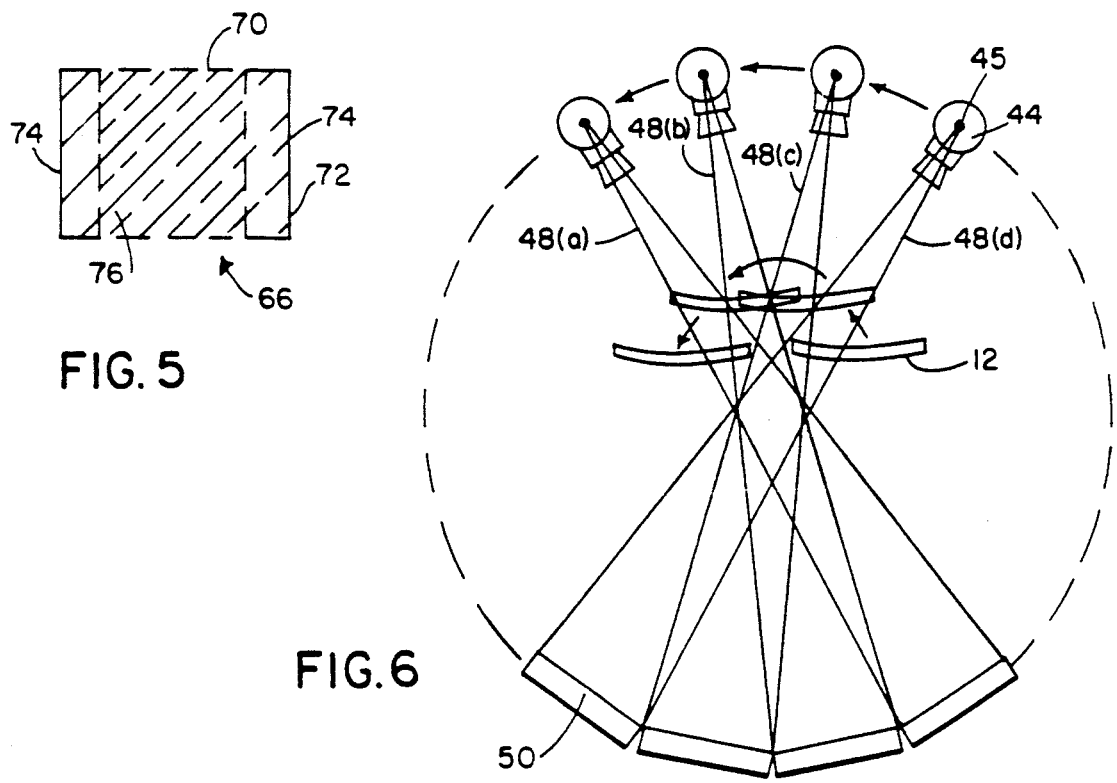
FIG. 5
FIG. 6

METHOD AND APPARATUS FOR PIECE-WISE RADIOGRAPHIC SCANNING

This application is a continuation-in-part of application Ser. No. 07/976,797 filed Nov. 16, 1992 and entitled: "Patient Positioning Apparatus for Bone Scanning" which is a continuation-in-part of application Ser. No. 07/944,626 filed Sep. 14, 1992 now U.S. Pat. No. 5,228,068 and entitled: "Method for Analyzing Vertebral Morphology Using Digital Radiography".

FIELD OF THE INVENTION

The present invention relates generally to radiographic instruments and more particularly to an apparatus for assembling broad area images from narrow beam radiographic scans.

BACKGROUND OF THE INVENTION

Scanning radiographic equipment differs from conventional radiography in that it employs a narrowly collimated beam of radiation, typically x-rays formed into, for example, a fan beam, rather than a broad area cone beam. The small beam size used in scanning radiographic equipment allows replacement of an image forming sheet of radiographic film, used with conventional radiographic equipment, with a small area array of detector elements.

The detector elements receiving the transmitted radiation produce electrical signals which may be converted to digital values by an analog to digital converter for the later development of an image or for other processing by computer equipment. The ability to quantify the measurement of the transmitted radiation, implicit in the digitization by the analog to digital converter, allows not only the formation of a radiographic "attenuation" image but also the mathematical analysis of the composition of the attenuating material by dual energy techniques. See generally, "Generalized Image Combinations in Dual KVP Digital Radiography", by Lehmann et al. Med. Phys. 8(5) September/October 1981. Such dual energy techniques quantitatively compare the attenuation of radiation at two energies to distinguish, for example, between bone and soft tissue. Dual energy techniques allow the measurement of bone mass, such measurement being important in the treatment of osteoporosis and other bone diseases.

The limited area of the beam of radiation used in scanning radiographic systems allows the use of limited area detectors permitting high resolution with relatively lower cost. The limited area of the detectors, however requires that the beam be scanned along several adjacent paths if large area images are to be constructed. Typically, a fan beam will be scanned in a raster pattern over the area to be measured, each line of the scan separated by somewhat less than the width of fan beam, to ensure complete illumination of the entire volume of the imaged object, with the directions of scanning being generally perpendicular to the direction of the radiation and the plane of the fan beam.

Images formed by a scanning radiographic system are potentially more accurate than those produced by a typical broad beam radiograph system. This accuracy arises from the limited divergence, in the scanning direction, of the rays of the fan beam, as compared to a broad area cone beam. This narrow collimation of the fan beam reduces "parallax" in the projected image, particularly of anatomical planar surfaces that are nearly parallel with the plane of the fan beam—such as the superior and inferior borders of the vertebrae in the spine when the scanning directions is along the superior-inferior axis of the body.

Morphological measurements of the vertebrae, and other structures, which benefit from reduced parallax are used to evaluate various dimensions of a vertebra to detect crushing or other deformation that are one element of certain bone diseases such as osteoporosis. See e.g. Minne et al., "A Newly Developed Spine Deformity Index (SDI) to Quantitate Vertebral Crush Factors in Patients with Osteoporosis," *Bone and Mineral*, 3:335–349 (1988); J. C. Gallagher et al, "Vertebral Morphometry: Normative Data," *Bone and Mineral*, 4:189–196 (1988); Hedlund et al, "Vertebral Morphometry in Diagnosis of Spinal Fractures," *Bone and Mineral*, 5:59–67 (1988); and Hedlund et al, "Change in Vertebral Shape in Spinal Osteoporosis," *Calcified Tissue International*, 44:168–172 (1989). Automatic techniques for morphological measurements of bone are described in U.S. patent application Ser. No. 07/944,626 filed Sep. 14, 1992 and entitled: "Method for Analyzing Vertebral Morphology Using Digital Radiography" assigned to the same assignee as the present application and hereby incorporated by reference.

Nevertheless, images developed with scanning fan beam equipment can include certain distortions or artifacts. In particular, it has been noted that objects at the interface between two adjacent scan paths contain a blurring or distortion in a direction perpendicular to the scan path.

SUMMARY OF THE INVENTION

The present invention provides a method and apparatus for constructing broad area images from a sequence of narrow fan beam scans. The invention recognizes that a source of image artifacts in combining narrow, fan beam scans is the varying amount of overlap between the fan beams when the axes of the fan beams are held parallel. This overlap causes some volume elements of the patient to be measured with rays at two different angles. The amount of overlap depends on the height of the structure being imaged, as measured along the path of the fan beams, and thus cannot, in general, be determined or corrected in a two dimensional image.

The present invention varies the angle of the axis of each fan beam so as to create a larger, effective fan beam of arbitrary width and to eliminate any height dependant overlap. The elimination of height dependent overlap ensures that each volume element of the patient is measured by rays at only one angle. Specifically, the invention employs an imaging system having a radiation source directing a fan beam of radiation toward the patient, where the fan beam diverges about a radiation axis, substantially within a beam plane, from a focal spot. A radiation detector opposing the radiation source along the radiation axis receives the diverging beam of radiation after passage through the patient to produce a projection signal indicating the attenuation of the beam of radiation for multiple rays within the beam.

The radiation axis may be moved along a first and second path across the patient, the first and second paths being spaced apart and substantially perpendicular to the beam plane. In moving between the first and second paths of the scan, the radiation axis is rotated about the focal spot by a displacement angle, within the beam plane. The signals obtained along the first and second path are then combined to produce a two dimensional projection image.

It is thus one object of the invention to reduce image artifacts, caused by combining image data obtained from multiple scannings of a narrow fan beam. Creating a larger, effective fan beam eliminates areas of overlap or produces areas of overlap that, with appropriate projections, are constant regardless of the height of the imaged structure, and which therefore can be eliminated by a constant weighting factor applied to the data of the overlapping area.

The radiation detector may be a linear array of detector elements, each subtending a first width of the fan beam along the linear array, where the projections signals include a plurality of elements signals from each detector element. A projector may be employed to map the element signals to pixels of a non-planar image surface generally normal to the radiation axis, each pixel subtending second widths of the fan beam varying from the first widths. The non-planar image surface may be positioned midway along the height of the patient as measured along the radiation access.

It is thus another object of the invention to reduce the distortion caused by the divergence of rays in both the narrow measuring fan beams and the larger, effective fan beam by mapping the element signals to pixels of a non-planar surface so that each such pixel represents rays of the fan beam passing through equal areas of the patient. This reduces variations, for example, in bone mineral density measurements, which are sensitive to distortion in the measured area.

It is another object of the invention to reduce the magnitude of magnifications induced errors on the projected image. By positioning the non planar image surface to approximately bisect the body, distance between the imaging plane and any particular structure in the body, such as affects magnifications, is reduced to a minimum.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

BRIEF DESCRIPTION OF THE DRAWINGS

FIG. 4 is a view in elevation taken along line 4—4 of FIG. 1 showing different positions of the radiation source and detector for a scanning pattern of FIG. 2(a) and regions of overlap between adjacent fan beam such as may cause artifacts in a composite image;

FIG. 5 is a simplified diagram of a composite image of a cubic volume positioned in the region of overlap of FIG. 4 having a superimposed dotted line circumscribing the structure's actual dimensions to show transverse distortion caused by the region of overlap;

FIG. 6 is a diagram similar to FIG. 4 showing positioning of the radiation source, radiation detector, and table of the densitometer of FIG. 1, exaggerated for clarity, to realize a larger, effective fan beam per the present invention;

DETAILED DESCRIPTION OF THE PREFERRED EMBODIMENT

Figure 1:
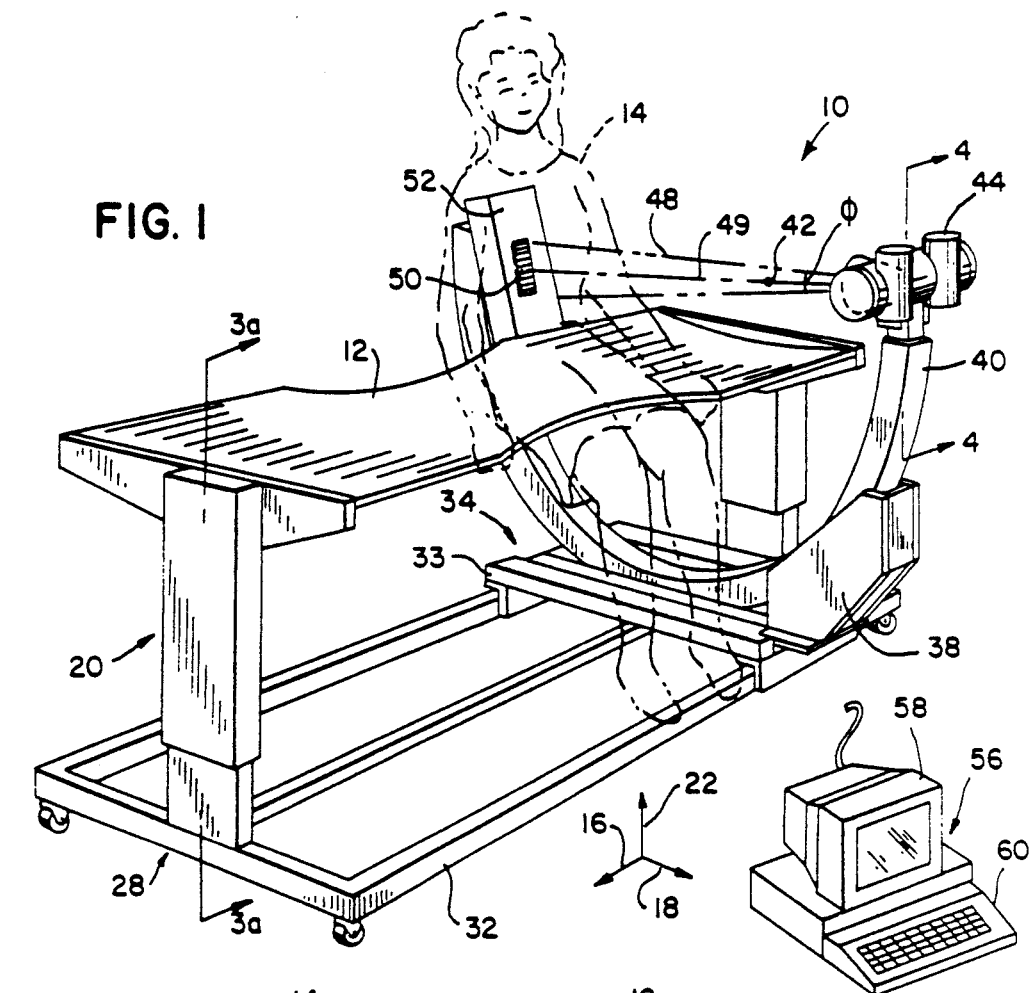
FIG. 1 is a perspective view of a densitometer per the present invention showing a C-arm, having an x-ray source and a detector, and a table positioned for holding a patient and a controlling computer.

Referring to FIG. 1, a bone densitometer 10 constructed according to the present invention includes a table 12 for supporting a patient 14 in a sitting position prior to and after an examination (as shown) or in a supine position along the table's longitudinal axis 16 during an examination. The table 12 is constructed of epoxy impregnated carbon fiber laminated over a foamed plastic core. This combination of materials is extremely light, and generally radiolucent and stiff. Further, the attenuation is extremely uniform so as to prevent the introduction of artifacts into the radiographic images. The table 12 has a generally linear cross-section along the longitudinal axis 16 and an upwardly concave cross-section along a transverse axis 18 perpendicular to the longitudinal axis 16. Thus, the table 12 is a trough-shaped sheet whose transverse curvature provides additional resistance to longitudinal bending.

Support pillars 20 hold either longitudinal end of the table 12. The support pillars 20 are separated by a distance greater than the typical height of the patients to be examined so that the support pillars 20 do not obstruct the scanning process nor attenuate the measuring radiation. The longitudinal stiffness of the table 12 allows it to bridge the distance between the pillars 20 as an unsupported horizontal span thereby eliminating additional radiation attenuating structure.

Figure 2A:
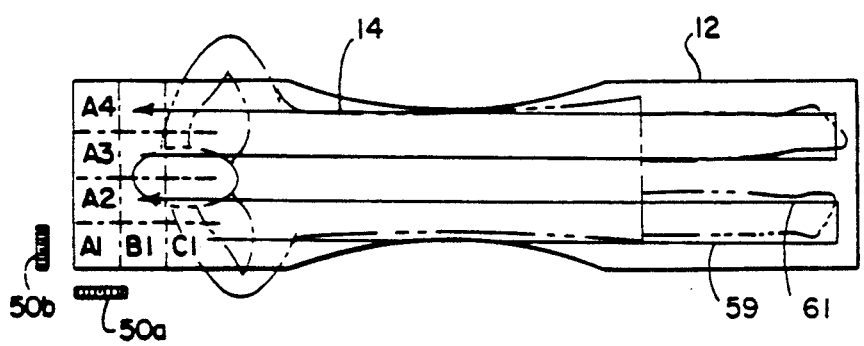
FIGS. 2(a) and 2(b) are plan and elevation views of the table of FIG. 1 showing the hourglass shape of the table and a typical scanning pattern that may be employed by the present invention.
Figure 2B:
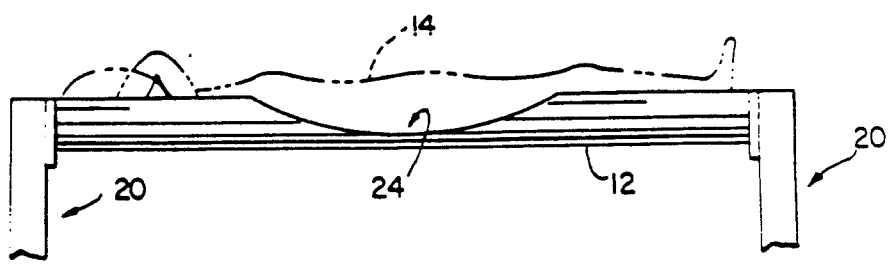

In one embodiment shown in FIG. 2(b) the transverse width of the table 12 varies along its longitudinal extent being widest near the support pillars 20, and thus near the head and feet of the patient 14 when the patient 14 is in the supine position on the table 12, and narrowest at the mid-portion of the table 12 corresponding generally to the area of the patient's vertebrae. This narrowing of the table 12 is in the form of two rounded notches 24 extending inward toward the center of the table from either transverse edge and imparting to the table an hourglass shape as viewed along a vertical axis 22 perpendicular to the longitudinal and transverse axes 16 and 18 respectively.

Figure 3A:
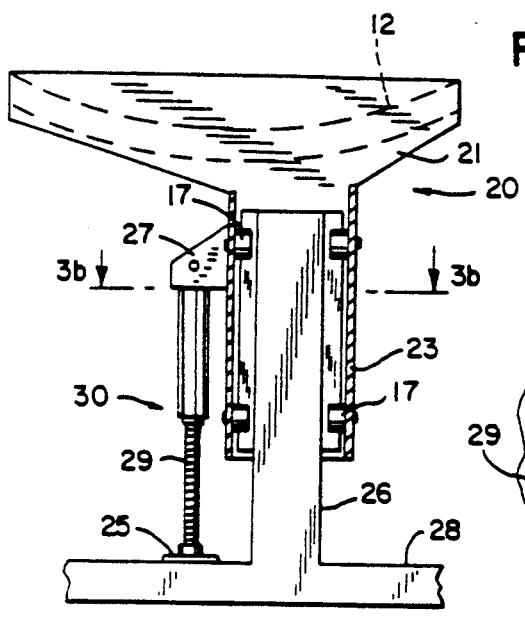
FIG. 3(a) is a cross-section of one support for the table of FIG. 1 taken along line 3(a)–3(a) in FIG. 1 showing the upward curvature of the table surface and the mechanism for elevating and lowering the table.
Figure 3B:
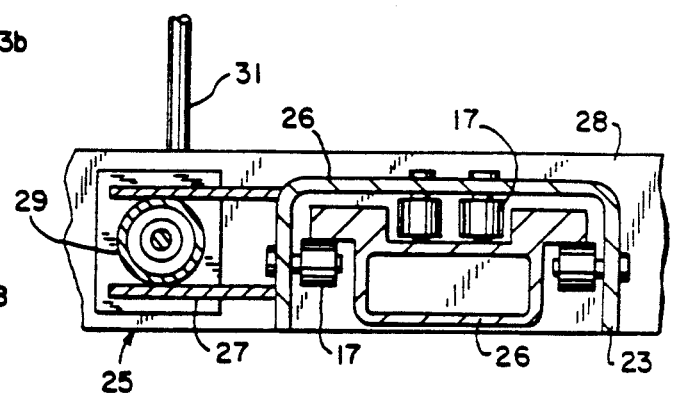
FIG. 3(b) is a cross-section of the support of FIG. 3(a) taken along line 3(b)–3(b) of FIG. 3(a)

Referring now to FIGS. 1, 3(a) and 3(b), support pillars 20 extend vertically downward around upward extending posts 26, the latter which are attached, at their bottom ends, to a bed 28 supporting the densitometer 10. The support pillars 20 each include a horizontal architrave 21, extending the width of the table 12 and attached to a respective end of the table 12, and vertical channel shaped casing 23 surrounding the posts 26 to vertically slide in engagement with the posts 26 guided by a set of rollers 17 attached to the casing 23. The casings 23, and hence the support pillars 20, may be positioned vertically as driven by actuators 30 each comprising a nut 27 attached to an outer casing wall and a lead screw 29 received at one end by the nut 27 and at the other end by a right angled drive 25 attached beneath the nut to the bed 28. A common drive shaft 31 connects each right angled drive 25 to a single stepper motor (not shown) so that rotation of the drive shaft 31 turns the right angled drives 25 and hence the lead screws 29 in tandem so as to raise and lower the table 12 on pillars 20 while maintaining the table's horizontal attitude. The number of steps made by the stepper motor is simply related to the change in table height.

Figure 3C:
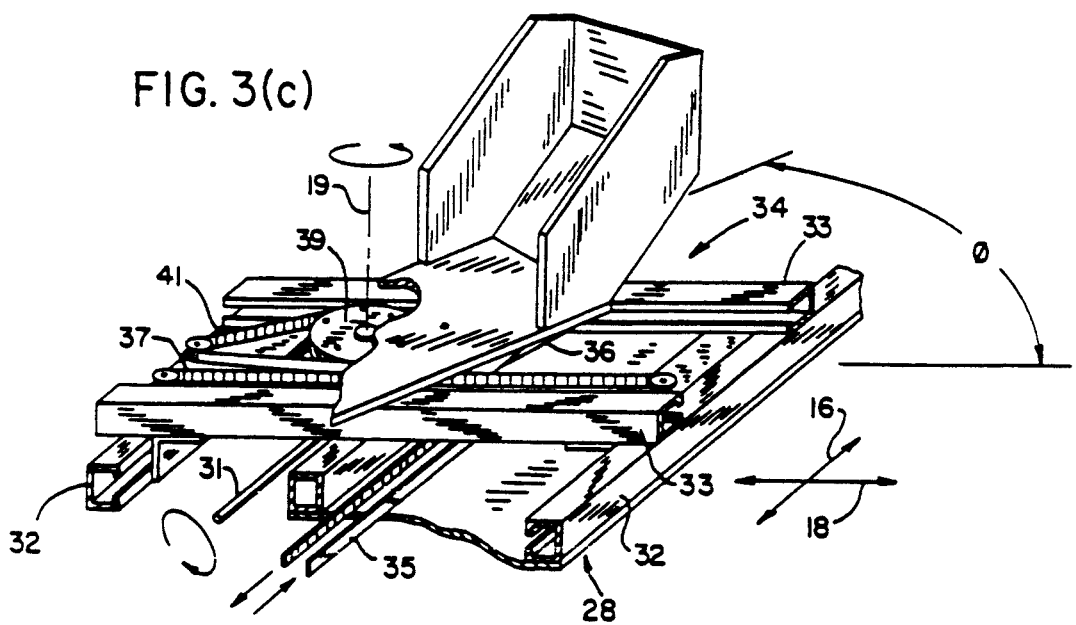
FIG. 3(c) is a perspective cutaway view of the supporting mechanism for the C-arm of FIG. 1 showing rotation of the C-arm with respect to the gantry pallet and the x and y translation of the pallet.

Referring to FIG. 1 and 3(c) the bed 28 includes two longitudinal rails 32 which form a track for supporting a transversely extending gantry pallet 34, and which allow the gantry pallet 34 to be positioned longitudinally along substantially the entire length of the densitometer 10 (as indicated by longitudinal axis 16).

The gantry pallet 34 includes transverse rails 33 carried by rollers (not visible) fitting within the rails 32 and motivated by a stepper motor driven flexible belt 35. Riding on the rails 33 of the gantry pallet 34 is a slider 36 moved transversely by stepper motor driven belt 37. The slider 36 supports a turntable 39 having a vertically oriented axis of rotation 19 and rotated by mean of stepper motor driven belt 41. As before, the stepper motors driving belts 35 and 37 allow a determination of the precise movement of their respective components through a tallying of the steps taken, as will be understood to those of ordinary skill in the art.

The turntable 39 supports a C-arm collar 38. Collar 38 is generally arcuate to enclose and slidably hold a C-arm 40 such that the ends of the C-arm may rotate about an isocenter 42 as the body of the C-arm 40 slides through the collar 38. The C-arm 40 is constructed as described in U.S. Pat. No. 4,955,046 to Aldona A. Siczek and Bernard W. Siczek entitled: "C-Arm for X-ray Diagnostic Examination". The C-arm 40 is motorized, as is understood in the art, to allow remote control over the positioning of the C-arm 40 in collar 38.

The radiation source 44, which is an x-ray tube, is mounted at one end of the C-arm 40 via a support beam 46 and is oriented to direct a polychromatic x-ray fan beam 48 along beam axis 49 generally towards the isocenter 42. The fan beam emanates from a focal spot 45 and diverges away from the beam axis 49 within a fan beam plane 57 to define a fan beam angle $\phi$.

The fan beam 48 is received by a linear detector array 50 extending perpendicularly to the fan beam axis 49, within the fan beam plane 57, and generally on the opposite side of the patient 14. The linear detector array 50 is comprised of a number of adjacent detector elements 47 each of which may detect the attenuation of one ray of the fan beam 48. The linear detector array 50 may be a scintillation type detector, as is understood in the art, having scintillation materials which convert x-rays to visible light to be detected by photodetectors which produce a corresponding electrical signal. Each detector element 47 of the detector array 50 incorporates two side-by-side scintillators and photodetectors to measure the x-rays fluence, of the polychromatic fan beam 48, in one of two energy bands and thus to provide, during scanning, a dual energy measurement at each point in the scan. As noted above, such dual energy measurements allow the tissue of the patient 14 being measured at a given point associated with a detector element 47 to be characterized as to its composition, for example, into bone or soft tissue.

The detector array 50 is affixed to a stop plate 52 and mounted to the opposing end of the C-arm 40.

Together, motion of the pallet 34 and slider 36 permit a scanning by the detector 50 and radiation source 44 of the densitometer 10, the scanning translating the beam axis 49 across the patient 14, whereas the motion of the turntable 39 (of FIG. 3(c)) allows for control of the angle of the fan beam plane 57 with respect to the patient 14, as will be described.

The motion of the slider 36 (shown in FIG. 3(c)) is not limited to providing a scanning motion but may be used, in conjunction with rotation of the C-arm 40 in collar 38, to provide improved imaging of specific structures in the body without disturbing the patient 14 from the supine position. For example, imaging of the femur 53 of a supine patient 14 is ideally done at an angle of approximately 20°-25° from vertical. In prior art devices this typically required uncomfortable inward rotation of the leg of the patient 14. The ability, in the present invention, both to rotate the C-arm 40 and to move the slider 36 along the transverse axis 18, and thus to move the isocenter 42, permits this imaging to be done without movement of the patient 14. Specifically, the desired angle of the C-arm 40 is simply selected and the slider 36 moved so that the beam axis 49 aligns with the femur 53. This and other aspects of the architecture of the densitometer 10 are discussed in the parent application Ser. No. 07/944,626 filed Sep. 14, 1992 and entitled: "Method for Analyzing Vertebral Morphology Using Digital Radiography", hereby incorporated by reference.

Combined motion of the C-arm 40, the slider 36, the pallet 34 and the table 12 permit the densitometer 10 to scan images not simply along the anterior/posterior and lateral directions, but at any angle of the C-arm 40. Each of these actions of the C-arm 40, the slider 36, the pallet 34, and the table 12 may be controlled by a computer 56 having a display terminal 58 and a keyboard 60 such as are well known in the art. By providing step commands to the motors associated with the various components above described, the computer 56 may control and locate these components, for example, by adjusting and tracking the height of the table 12, through actuators 30. The computer 56 also turns the radiation source 44 on and off and importantly collects digitized attenuation data from the individual elements of the linear detector array 50 to generate a matrix of measured data elements over the patient 14.

Referring now to FIGS. 2(a) and 4, radiation source 44 and the detector array 50 may be positioned with respect to collar 38 so that the beam axis 49 is substantially vertical. For a whole body scan of a patient 14, the detector array 50 can be oriented transversely as indicated by 50(b) so as to scan longitudinally as indicated generally by the sequence of areas A1, B1 and C1 from the patient's head to the patient's foot. During this scanning, the fan beam axis 49 traces a first path 59. At the end of this scan, a second longitudinal row of data would be taken conforming generally to the sequence of areas A2, B2 and C2 with fan beam axis tracing along second path 61, from the patient's foot to the patient's head. Four to five such longitudinal rows may be required for a full body scan.

Typically, at the conclusion of the scan of the first path 59, following the sequence A1, B1, C1 . . . , both the radiation source 44 and detector array 50 would both be moved transversely so that the fan beam axis 49, still vertical, intercepts the second scan path 61. The fan beam axis 49 as so displaced is designated 49', and is moved transversely by an amount equal to the transverse width (measured within the fan beam plane 57) of the fan beam 48 as it enters the patient 14. This displacement, which is generally smaller than the fan beam width as it exits the patient 14, ensures that all volumes of the patient 14 are illuminated in one of the several longitudinal paths of the whole body scan. This scanning procedure, however, will also produce a triangular overlap area 69 of redundant measurement between fan beams on paths 59 and 61 and will cause certain volume elements of the patient within that area 69 to be illuminated twice and hence measured twice during the scanning. For example, vertically aligned cubic volume elements 66, 67 and 68 within the patient 14 and approximately half-way between scan paths 59 and 61 will be scanned during motion along both scan paths 59 and 61.

Referring now also to FIG. 5, this dual measurement of volume elements 66–68 will in general cause a transverse spatial distortion in the image of these structures. This distortion arises from the different angles of the measuring rays and, in general, the lack of information as to the height of the volume elements 66–68 within the patient 14. When the data of the individual scans along paths 59 and 61 are simply combined, the uncertainty in height of the volume elements 66–68 translates to an uncertainty in transverse position, and the image exhibits a transverse spreading or smearing. For example, if an image is projected to an imaginary plane at the height of the upper surface of the detector array 50 (a default image plane if the raw data from the detector array is otherwise unprocessed), then cubic volume element 66 having true projected outline 70 will project to a rectangular element 72 having wing portions 74 of lower density than a central portion 76.

In addition to the spatial distortion caused by the multiple measurements in area 69, the redundancy of the data will distort the absorption values associated with the points of the projected image. The image's central portion 76, for example, will be the sum of two measurements of volume element 66 whereas the wing areas 74 will be only one measurement of volume element 66. In theory, this error can be corrected by a weighting of the projection data so that the effect of the redundancy is eliminated, however, again because the height of the volume element 66 is not known, an accurate weighting system cannot be derived. In general, height information is not available in a two-dimensional projection.

The present invention recognizes that the distortion of FIG. 5 is not simply due to the overlapping of fan beams 48 along adjacent scans but rather because of the variation in overlap as a function of height within the patient 14. Accordingly, the present invention provides a method of orienting the fan beam axis 49 for the scanning of multiple longitudinal columns so that the overlap, if any, is constant along the length of the fan beam axis 49.

Figure 7:
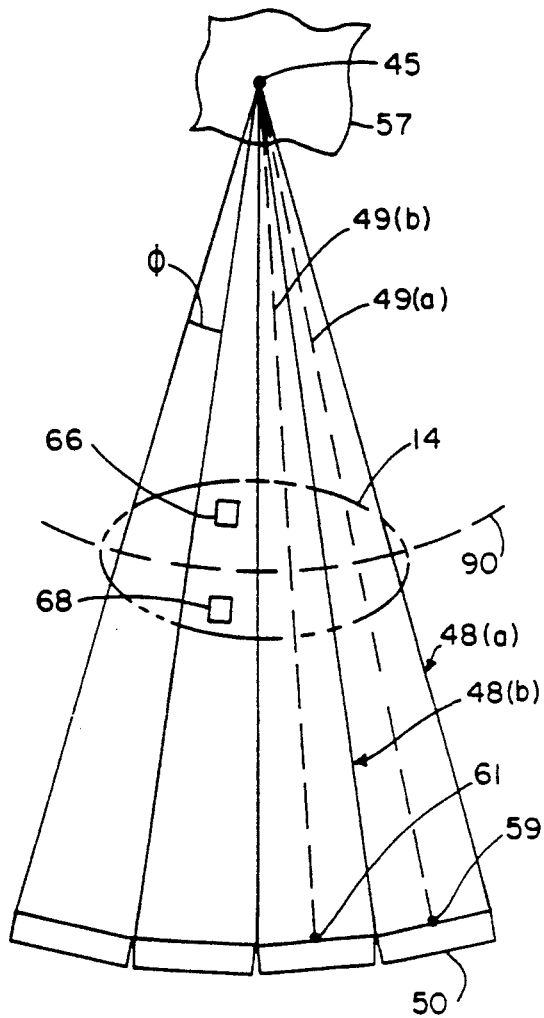
FIG. 7 is a diagram similar to FIG. 6, but from a view point on the table, showing the combination of the beams generated per FIG. 6 to form the larger, effective fan beam received by the linear radiation detector as moved to a variety of corresponding positions with no overlap.

Referring now to FIGS. 6 and 7, this requirement of constant overlap between fan beams 48 of scans of adjacent columns of the patient 14 requires the edges of the fan beams, opposed about the fan beam axes 49 within the beam plane 57, be parallel, and most simply abut one another. As shown in FIG. 7, if the fan beam 48 associated with scan path 59 is designated 48(a) and its axis 49(a) and the fan beam 48 associated with scan path 61 is designated 48(b) and it axis 49(b), and so forth for the remainder of the fan beams 48 employed in the whole body scan of patient 14, then each of the successive axes 49 will be displaced about the focal spot 45 by exactly $\phi$, the fan beam angle, and the edges of the adjacent fan beams will just abut when viewed from the perspective of the patient 14 and the table 12. In this case the focal spot 45 for each of the fan beams 48(a)–(d) is the same (with respect to the position of the table 12) for each scan, or more precisely, does not move along the fan beam plane 57 with respect to the table 12.

Figure 11:
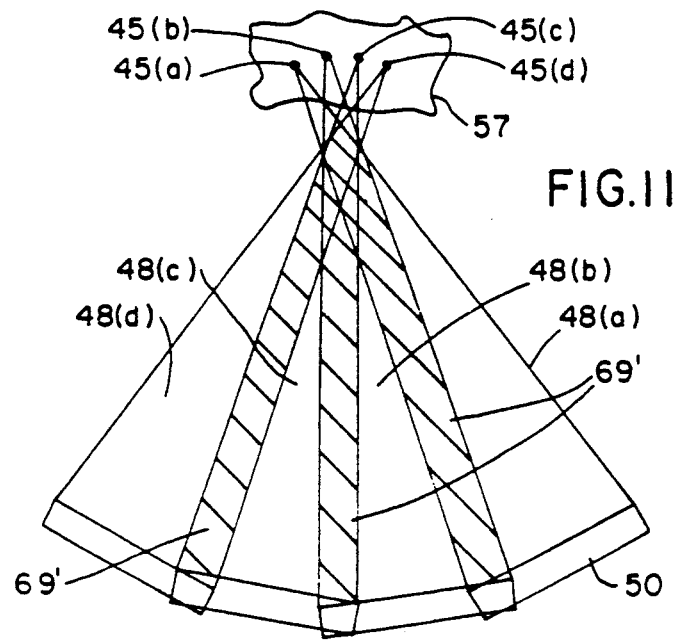
FIG. 11 is a figure similar to that of FIG. 7 showing an effective fan beam with constant overlap between the fan beams.

Alternatively, as seen in FIG. 11, the edges of the fan beams 48(a)–(d) may overlap slightly but by a constant width. Again, each of the successive axes 49 for the fan beams 48(a)–(d) will be displaced angularly by exactly $\phi$ the fan beam angle, but the focal spots 45(a)–(d), for each fan beam 48(a)–(d), respectively, will no longer be fixed in the table reference frame. Nevertheless, because the amount of overlap is unvarying as a function of distance along the fan beam axis 49, using the appropriate projection and weighting process, as will be described, image artifacts caused by the overlap may be removed. Although the areas of overlap 69' are of constant thickness, they change in transverse location depending on the height of the beams in the patient 14. This would seem to raise the same problem of height dependance caused by triangular areas of overlap 69 of FIG. 4, however, the height dependance can be eliminated for constant thickness overlap areas 69' by the proper choice of a projection plane, as will be described below.

In both of the cases of FIGS. 7 and 11, the fan beams 48(a)–(d) are combined to realize an effective, larger fan beam. In the case of FIG. 11, the projections in the area of overlap must be weighted to prevent the redundant data from having a disproportionate effect on the composite projection image. This weighting may be, at a minimum, simply discarding one set of redundant data (a weighting of zero) or by giving the two sets of data a pair of weights that sum to one. At present, the possibility of patient motion, makes no overlap or the discarding of overlap data preferred, because a weighting and combining blurs the image and is less preferred for diagnosis than some mis-registration in the combined image.

Further, it will be recognized that the amount of overlap must be kept small, even if there is no height dependence, because the important condition is that the rays measuring each volume element of the patient be at one angle, and the rays of the overlapping edges of the fan beams will have approximately the same angle only for small amounts of overlap.

Referring now to FIG. 6, although the effective larger fan beam may be assembled from fan beams 48(a-)-(d) in a straightforward way in the reference frame of the table 12, the actual motion of the C-arm 40, the table 12 and the slider 36 and pallet 34 of the densitometer 10 in the reference frame of the room is more complex. The angle of the fan beam axes 49(a)-(d) may be achieved simply by rotating the C-arm 40 within its collar 38. However, generally, this rotation will change the height of the focal spot 45 with respect to the table 12 and will change the transverse location of the focal spot 45 with respect to the table 12. Accordingly, compensatory motion of the table 12, up or down and transversely, will need to be performed. The proper orientation of the fan beams 48(a)-(d) is thus performed by a set of motions of the various components of the densitometer 10 working together under the control of computer 56.

It should be noted that the effective wide area fan beam might be expected to produce considerable spatial distortion if used with a single linear detector array spanning the entire effective fan beam (or if the detector array 50 were simply translated along a line beneath the effective fan beam) Such distortion would be caused by the increasing distance between the focal spot 45 and the elements of the detector array 50 for the edgemost rays of the effective fan beam. An increase in distance causes an increased magnification of the image received by the detector array 50 which can also affect quantitative measurements such as bone density to be described below. Nevertheless, the present invention avoids this extreme distortion by piecewise approximating a curved detector (of constant distance from the focal spot for the entire effective fan beam) by means of the short segments of the actual detector array 50.

Nevertheless, each short segment 50 still deviates from a true curved detector and thus, the detector elements of each detector 50 have varying distances from the effective focal spot 45 of the composite fan beam. This deviation can be corrected in the projection process of the present invention, as will be described.

Figure 8:
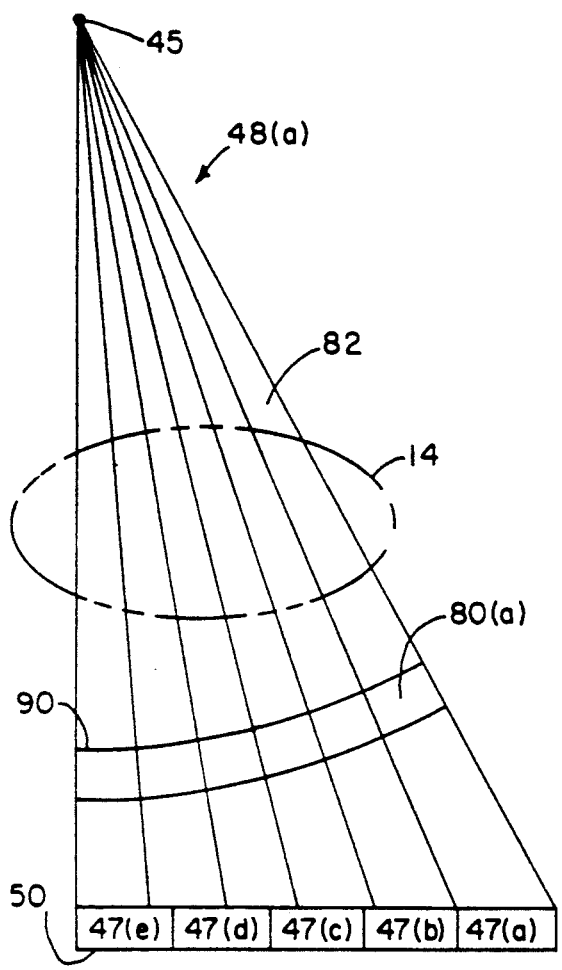
FIG. 8 is a detailed view of a fan beam received by the linear radiation detector showing the mapping of rays of radiation within equal angled intervals to the surfaces of the linear radiation detector and to a curved image surface.

Referring to FIG. 8, a fan beam 48(a) of the effective fan beam includes a number of rays 82 comprising adjacent triangular zones of equal angle about the focal spot 45. To a first approximation, each ray 82 measures a equal area of the patient 14. Ideally, then, each ray 82 should map to a single picture element (pixel) of a two-dimensional projection image constructed of the data collected in the scan. This mapping of rays 82 to pixels, preserves the local spatial fidelity of the image and prevents distortion in the quantitative values assigned to each pixel such as may be area sensitive. For example, if the attenuation of the energy of the fan beam 48 by the patient 14 indicates bone mineral content (BMC) in grams, the diagnostically useful quantity of bone mineral density (BMC) in g/cm$^2$ requires an accurate preservation of area information. This equal area pixel mapping is advantageous in the measurement of BMD.

Nevertheless, the spatial periodicity of the rays 82 will not in general match that of the detector elements 47 of the detector array 50. For example, if the outermost ray 82 of a fan beam 48(a) exactly subtends the outermost detector element 47(a) of the detector array 50, a more centrally located ray 82 will subtends less than the area of a more centrally located detector element 47(e). If the raw data from the detector elements 47 is directly mapped to pixels of an image, area distortion will occur. Further, the distance of the outermost detector elements 47(a) from the focal spot 45 will typically be greater than that of the more centrally located detector elements 47(e). This distance variation will cause magnification distortion, as generally discussed above.

Figure 9:
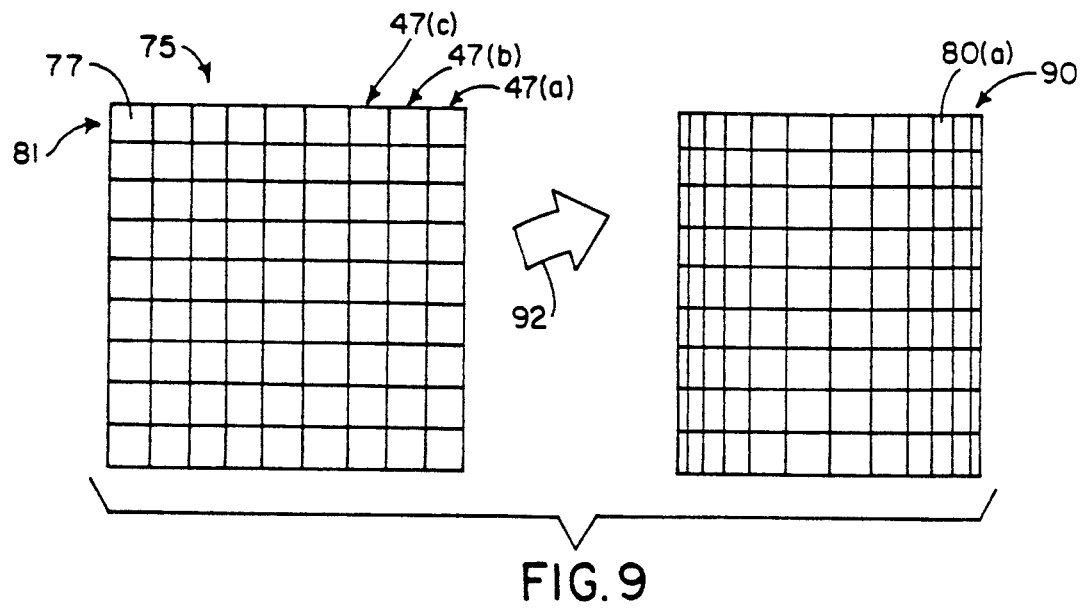
FIG. 9 is a schematic representation of the processing of the raw data image collected by the radiation detector as mapped to the imaginary curved image surface of in FIG. 9.
Figure 10:
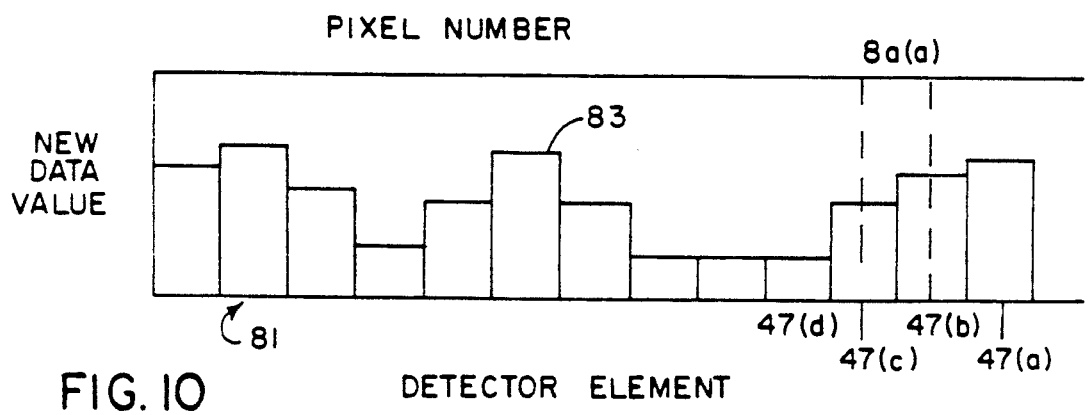
FIG. 10 is a graph of a simplified projection signal as received by detector elements of the radiation detector showing the mapping of the projection signal to the pixels of the curved image surface.

Accordingly, referring also to FIGS. 9 and 10, the data obtained from each detector element 47 is adjusted by a projection process to pixels in a non-planar image surface. During the scanning process, the data from each detector element 47 of the detector array 50 is collected in a matrix 75 having elements 77 associated with a given coordinate in the scan (with respect to the table 12) and a row and column in the matrix 75. Generally the rows of the matrix 75 will correspond to variations in the transverse coordinate of the data of the scan, and the columns will correspond to variations in the longitudinal coordinate of the data of the scan. A single row 81 represents the data for one position of the effective fan beam and the values of the data of that row 81 provide a projection signal 83. The value of the projection signal 83 is a stepwise continuous function of the number of the detector element.

Referring to FIGS. 8 and 10, the projection signal 83 may be projected to a curved image surface 90 having pixels 80 exactly subtending one ray 82 each. This mapping 92 is accomplished by partitioning the projection signal 83 according to the geometric relationship between the pixels 80 of the curved image surface 90 and the detector elements 47. For example, pixel 80(a) spans the projection signals produced by detector elements 47(c) and 47(b). Accordingly the value of pixel 80(a) is simply the average value of the detector signals within the span or a weighted average of the values of the projection signals 83 for detector elements 47(c) and (d) in proportion to how much they are overlapped. This projection process is repeated for each pixels 80 of the image surface 90 until all the data has been projected.

If a curved image surface 90 is adopted equal to the radius of curvature focal spot 45 for that image surface 90, then moving the image surface 90 up and down along the fan beam axes 49 is simply a uniform scaling of the image. Preferably, the absolute height of the image surface 90 will be selected to approximately bisect the height of the patient 14. This will reduce the magnitude of the magnification error in the image caused by the diverging rays 82 of the fan beams 48 by reducing the absolute value of the distance between volume elements 66–68 of the patient 14 from the image surface 90. The use of a image surface 90 curved about the focal spot 45 also eliminates height dependency of the areas of overlap 69' as discussed with respect to FIG. 11, because in the projection geometry the overlap will have constant transverse location in the image surface 90.

Referring now to FIG. 10, in an anterior/posterior scan of the patient 14, where the fan beam axis 49 is oriented vertically, the data of a rectilinear matrix 75 of data elements 77 is acquired. Each element 77 of the matrix 75 has a location corresponding to a particular path of a ray of the fan beam 48 through the patient 14, and to one detector element 47 of the detector array 50, and each data element 77 has a value related to the attenuation of that ray as it passes through the patient 14. As is understood in the art, the computer 56 stores the pixel values and their relative spatial locations so that each data element 77 may be readily identified to the particular area of the patient 14 at which the data of the data element 77 was collected.

According to well understood dual energy imaging techniques, the value of each data element 77 is derived from measurements of the patient at two energy levels and thus provides information indicating the composition of the material causing that attenuation. In particular, the data element value indicates the bone mineral content of the volume of the patient corresponding to the data element location.

The above description has been that of a preferred embodiment of the present invention. It will occur to those that practice the art that many modifications may be made without departing from the spirit and scope of the invention. In order to apprise the public of the various embodiments that may fall within the scope of the invention, the following claims are made.

We claim:

1. An imaging system for obtaining diagnostic images of a patient comprising:
    a radiation source for directing a fan beam of radiation toward the patient, the fan beam diverging about a radiation axis but substantially within a beam plane from a focal spot;
    a radiation detector opposing the radiation source along the radiation axis for receiving the diverging beam of radiation after passage through the patient to produce a projection signal indicating the attenuation of the beam of radiation for multiple rays within the beam;
    a translating means for translating the radiation axis along a first and second path across the patient, the first and second paths being spaced apart and substantially perpendicular to the beam plane;
    a repositioning means for rotating the radiation axis about the focal spot by a displacement angle, within the beam plane so as to move the radiation axis from the first path to the second path; and
    means for combining the projection signal obtained along the first and second path to produce a two dimensional projection image.

2. The imaging system of claim 1 wherein the repositioning means rotates the displacement axis without displacement of the focal spot within the beam plane with respect to the patient.

3. The imaging system of claim 1 wherein the fan beam has a fan beam angle measured within the beam plane and the repositioning means rotates the displacement axis by the fan beam angle.

4. The imaging system of claim 1 wherein the radiation detector is a linear array of detector elements, each subtending a first width of the fan beam along the linear array, and wherein the projections signals includes a plurality of elements signals from each element, the imaging system including:
    a projector for mapping the element signals to pixels of a non-planar image surface generally normal to the radiation axis, each pixel subtending second widths of the fan beam varying from the first widths.

5. The imaging system of claim 4 wherein the non-planar image surface is a section of a cylinder having a constant radius equal to the distance between the surface and the radiation source to substantially bisect the patient.

6. An imaging system for obtaining diagnostic images of a patient comprising:
    a radiation source for directing a fan beam of radiation toward the patient, the fan beam diverging about a radiation axis but substantially within a beam plane from a focal spot;
    a linear array of detector elements opposing the radiation source along the radiation axis, each detector element subtending a first width of the fan beam along the linear array, the linear array for receiving the diverging beam of radiation after passage through the patient to produce a projection signal which includes a plurality of element signals corresponding to the detector elements and indicating the attenuation of the beam of radiation for given rays within the beam; and
    a projector for mapping the element signals to pixels of a non-planar image surface generally normal to the radiation axis, each pixel subtending second widths of the fan beam varying from the first widths.

7. The imaging system of claim 6 wherein the non-planar image surface is a section of a cylinder having a constant radius equal to the distance between the surface and the radiation source the radius selected to substantially bisect the patient.

* * * * *